United States Patent [19]

Rothemund

[11] Patent Number: 4,459,247

[45] Date of Patent: Jul. 10, 1984

[54] METHOD FOR PRODUCING EARPLUGS OF FOAMED PLASTIC

[75] Inventor: Karl Rothemund, Schönwald, Fed. Rep. of Germany

[73] Assignee: Rehau Plastiks AG & Co., Rehau, Fed. Rep. of Germany

[21] Appl. No.: 353,954

[22] Filed: Mar. 2, 1982

[30] Foreign Application Priority Data

Mar. 5, 1981 [DE] Fed. Rep. of Germany ....... 3108261

[51] Int. Cl.³ ............................................. B29D 27/00
[52] U.S. Cl. .................................... 264/22; 128/152; 264/45.3; 264/45.5; 264/54; 264/145; 264/235; 264/346; 264/DIG. 5; 264/DIG. 18; 521/96; 521/154
[58] Field of Search .............. 128/152; 264/DIG. 18, 264/54, 22, 45.3, 145, DIG. 5, 235, 346, 45.5; 521/154, 96

[56] References Cited

U.S. PATENT DOCUMENTS

| | | | |
|---|---|---|---|
| 2,460,795 | 1/1949 | Warrick | 521/154 X |
| 3,271,332 | 9/1966 | Bond et al. | 521/154 |
| 3,344,220 | 9/1967 | Cook | 128/152 X |
| 3,429,838 | 2/1969 | Hersh | 521/154 |
| 3,565,858 | 2/1971 | Kniege et al. | 521/154 X |
| 3,677,981 | 7/1972 | Wada et al. | 521/154 X |
| 3,701,753 | 10/1972 | Shaw | 128/152 X |
| 4,026,846 | 5/1977 | Kittle et al. | 521/154 X |
| 4,160,449 | 7/1979 | Wade | 128/152 |
| 4,340,709 | 7/1982 | Jeram et al. | 264/328.6 X |

FOREIGN PATENT DOCUMENTS 2038543 2/1971 Fed. Rep. of Germany .
2251774 5/1973 Fed. Rep. of Germany .

OTHER PUBLICATIONS

*Chemical Abstracts,* vol. 87, 1977; No. 87:185850q: Ito et al., 77–81378, 7/77, "Silicone Rubber Foams," (p. 64).

*Primary Examiner*—Philip E. Anderson
*Attorney, Agent, or Firm*—Spencer & Frank

[57] ABSTRACT

The invention relates to an earplug, produced with the use of a polysiloxane which is made foamable and cross-linkable by the use of expanding and cross-linking agents. The method for producing such an earplug comprises preshaping the polysiloxane together with the additives, then finally shaping the earplug in the foaming process and then tempering the finally shaped product.

19 Claims, 1 Drawing Figure

| Mixing of Starting Materials | a) Polysiloxane<br>b) Cross-linking agents<br>c) Foaming agents<br>d) Additives |
|---|---|
| Preshaping | Extrusion |
| Foaming to Final Shape | Foaming and cross-linking to achieve final shaping (e.g. at 90 to 160°C) |
| Tempering | Tempering at at least 140°C, e.g. at 180°C for 6 hours. |

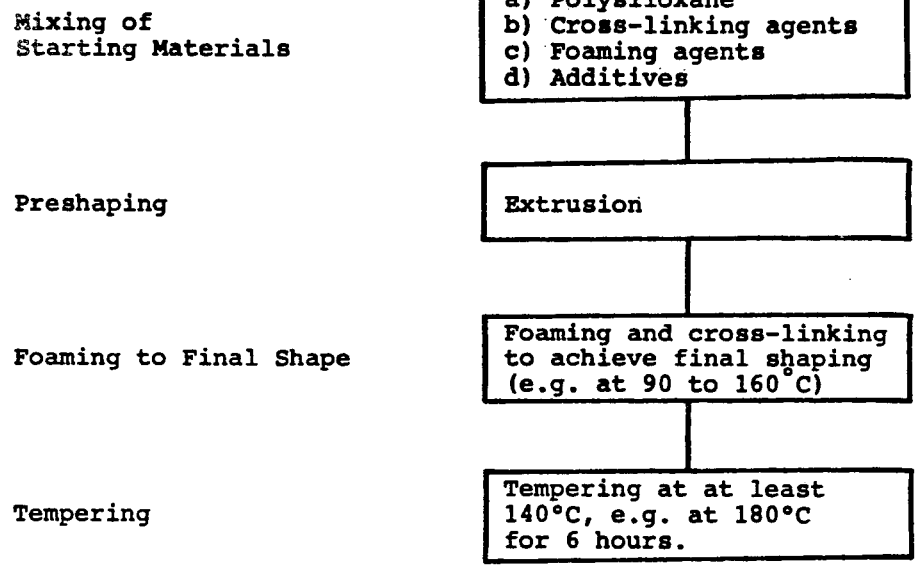

METHOD FOR PRODUCING EARPLUGS OF FOAMED PLASTIC

BACKGROUND OF THE INVENTION

A number of hearing protection elements are known which are introduced into the human ear passages in order to prevent or damp health endangering noise. Simple cotton wool is used for this purpose as well as cotton wool fibers which are impregnated with waxlike substances having kneadable properties.

German Offenlegungsschrift [patent application published without examination] No. 2,251,774 discloses a hearing protection element of a foamed polymer material which, due to its special foam structure, can be compressed by the use of pressure and can be introduced into the ear passages in this compressed state. Due to the slow recovery capability of the compressed, foamed polymer, the element, when inserted into the ear passage, will recover its shape after a short time so that the outer contours of the element place themselves against the surfaces of the ear passage and in this way provide a seal which reduces or prevents the penetration of health endangering noise into the interior of the ear passages. This prior publication indicates that any desired, flexible polymer material which can be foamed can be used to produce such an earplug. The essential criterion for this is seen to be that the data given in this prior publication regarding the pressure required for compression and the recovery rate of the foamed polymer must be maintained.

The prior publication employs vinyl chloride plastisol mixtures, foamable polyvinyl chloride plastisol mixtures and polyvinyl chloride mixtures. These are mixed with softeners and expanding agents to produce an appropriately foamed, disc-shaped product out of which are then cut the individual earplugs.

The particular advantage mentioned in the prior publication is that in this way, compressible, plug-like ear protection elements are produced which, due to their compressibility, are adaptable to the size and shape of any human ear passage. The prior publication considers this advantage to be so significant that it states that it is impossible to produce an earplug having a universally applicable size and shape out of a molded elastomer material. Due to their high elasticity, such materials are indicated to be unsuitable for the production of earplugs. In the opinion of the authors of this prior publication, the quick recovery property in particular impairs suitable introduction of the earplug into the ear passage.

The drawback of the prior art embodiments is that the foamable polymers employed, e.g. soft polyvinyl chloride as well as polyurethane etc., contain low molecular softeners, stabilizers or other processing residues which cannot be removed from the finished earplug. These components are not removable and may lead to skin irritations, contact dermatitis or other allergic skin reactions if used as earplugs, i.e. after the earplug has been inserted into a human ear passage. Since the foamable polymer of the prior publication is first brought into a disc shape and the actual plug shape is obtained only afterwards by cutting, stamping or similar mechanical work, there arises the additional drawback that the surface of these plugs is inevitably porous. This inevitably produces a certain chafing effect between the surface of the plug and the surface of the ear passage so that the above-mentioned negative influences on the skin are further supported thereby.

A further drawback is the susceptibility of the foamed polymers employed to the attack of microorganisms, such as fungi, bacteria etc. This susceptibility is known in particular for soft polyvinyl chloride while in connection with the use of polyurethane foams bacterial decay plays a special role. Moreover, at temperatures as they occur in the human ear passages, these damaging fungi, bacteria etc. encounter optimum growth conditions which can again enhance infectious reactions in the ear passage. This effect is further augmented by the porous surfaces of the prior art earplugs as a result of their manufacture and this additionally constitutes a significant contributing factor to easy soiling of the plug during use.

U.S. Pat. No. 4,160,449 discloses an earplug whose reboundable plug material consists of foamed silicone which, for hygienic reasons, is coated with a thin plastic foil. The encasing in a plastic foil is necessary because plugs cut out of foamed disc material or cut off from foamed rod material have coarse pores or open cells, at least at the cut portions, and thus may bring about disadvantageous skin irritations or allergic skin reactions.

SUMMARY OF THE INVENTION

It is a primary object of the present invention to avoid the above-mentioned drawbacks and to provide a method which produces a physiologically perfect earplug without additional auxiliary means. The invention achieves these and other objects in that initially the polysiloxane is mixed with the additives and is preshaped whereupon the final shaping is effected by the foaming process and the product is cross-linked in its final shape and that finally the product in its final shape is subjected to a final tempering process.

BRIEF DESCRIPTION OF THE DRAWING

The sole drawing FIGURE schematically illustrates an exemplary process route in accordance with the present invention.

DETAILED DESCRIPTION OF THE INVENTION

The invention employs an elastomer starting material which, due to the addition of expanding agents and cross-linking agents, is imparted special properties. Moreover, if required, appropriate fillers may be incorporated into the plastic starting material.

The expanding agents employed here may be chemical substances which decompose under the influence of temperature while giving off gases, such as, for example, azodicarbonamide, benzene sulfohydrazide, diphenyl sulfone-3,3 disulfohydrazide, diphenylene oxide-4,4 disulfohydrazide, trihydrazionotriazine, p-toluene sulfonyl semicarbazide, 5-phenyltetrazole, isatoic acid anhydride, sodium bicarbonate, etc.

However, physical expanding agents which evaporate under the influence of heat and thus expand can also be used. For cross-linking, radical forming cross-linking agents, in particular benzoyl peroxide, chlorobenzoyl peroxide, dichlorobenzoyl peroxide, t-butyl perbenzoate, dicumyl peroxide or di-t-butyl peroxide, are added to the polysiloxanes. However, cross-linking can also be effected by addition cross-linking or by means of a condensation reaction with discharge of water, acetic acid or amines at room temperature or in heat. Single or multicomponent systems can here be used and—seen as a whole—the cross-linking can be effected continuously or discontinuously.

In addition to the above-mentioned types of cross-linking, the cross-linking reaction can of course also be effected by the introduction of high energy radiation.

As fillers, the proposed polysiloxane may contain soots as well as inorganic fillers, particularly light-colored, inactive or semiactive, reinforced fillers. These may include oxidic or salt-like compounds of calcium, barium, magnesium, aluminum, silicon, titanium, iron, zinc or zirconium. Advantageously, the entire circumference of the individual particles of these fillers is enclosed by the polysiloxane, thus producing optimum surface characteristics in the final product.

A typical siloxane compound of the type employed here is represented by the following formula:

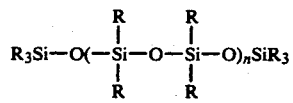

where R is an organic radical, particularly a methyl, phenyl, vinyl group, Si=silicon and O=oxygen.

The processing of this basic polymer into an earplug is not possible at all without cross-linking. While the prior art rejected the direct use of such cross-linked polymers for this purpose due to its negative characteristics—high elasticity and fast recovery—the invention adds special additives to the basic polymers, and employs a special temperature curve during the cross-linking process and during the subsequent tempering process with the aim of producing an end product of cross-linked polysiloxane which, due to its characteristics, such as great recovery capability and a relatively slow recovery time as well as a closed surface, can be used directly for earplugs.

A recipe that can be used according to the invention may have the following composition:
70 parts by weight dimethylpolysiloxane
30 parts by weight pyrogenic silicic acid
3 parts by weight azodiacarbonamide
1 part by weight dichlorobenzoyl peroxide Components according to the above exemplary recipe were intimately mixed together and introduced into a shaping process. Then the preshaped intermediate product was heated at about 210° C. for a period of 5 minutes, was thereby given its final foam shape and was simultaneously cross-linked. Thereafter, the cross-linked end product was tempered at about 180° C. for a period of 6 hours. In this way, a physiologically unobjectionable end product was obtained which was suitable for use as an earplug.

The end product is distinguished by a very good recovery capability. Moreover, it must be considered to be surprising that in spite of the material employed it was possible to realize a slow recovery time which, inter alia, is what makes the product suitable for this purpose. The particular properties of the end product according to the invention were tested in that the equilibrium pressure and the recovery time of an ear plug according to the invention were measured.

The equilibrium pressure was tested by reshaping the cylindrical test body in the radial direction, with the stated values having to be considered as the averages of various individual measurements. A test body was employed which had a diameter of 11.1 mm and a length of 16.3 mm. The deformation rate was 20 mm/minute, the deformation force was around 70%. The averages realized thereby were as follows:
deformation: 20.8 N
equilibrium pressure: 0.062 N/mm$^2$
hysteresis: 56.8%

The recovery time of a test body was determined as follows: the test body was stressed radially by a weight of 5 kg for a period of 30 seconds. The test body required 49 seconds to recover 90% of its original diameter.

With the use of the described polysiloxane, the special temperature resistance of the resulting products is given. According to the invention, the foaming and cross-linking temperature of the material may lie below 250° C., preferably between 90° C. and 160° C. This alone excludes the use of the foamable polymers disclosed in German Offenlegungsschrift No. 2,251,774. The thermoplastic polymers employed there receive their special characteristics from their reversible shaping, while the cross-linked polymers of the invention do not possess this reversibility, but are in their final state after the process according to the invention has been performed. This reversibility does not exist even if, according to the invention, the finally shaped product is subjected to a tempering process of at least 140° C. Moreover, the temperature resistance of the final product according to the invention has the result that these products can be sterilized repeatedly by boiling, by treatment with hot steam, hot air etc. This also indicates that the soft, foamable polymers according to the prior art are not suitable for the process according to the invention. Rather, in these polymers, the softeners and other additives required to make them soft and their harmful residues remain in the end product while in the invention similarly harmful residues are removed from the end product by the cross-linking process and the subsequent tempering process. Foreign matter absorbed later during use can be removed by sterilization.

According to the process of the invention, the polysiloxane is initially preshaped together with the additives. The desired final shape can here already be considered, which may produce, for example by way of deformation by means of extrusion, a round or oval, bar-shaped preliminary product.

It is within the scope of the invention for such a preliminary product to be subsequently given its final foamed shape, for example, by the introduction of heat. This may produce the smooth and nonporous surface of the end product. At the same time, this introduction of heat may effect the cross-linking. For cross-linking by means of high energy radiation—and that also is within the scope of the invention—the preliminary foaming and the final foaming of the product will be performed first before the end product is exposed to the high energy radiation. However, in this case, the preliminary foaming may be omitted and the foaming process may be conducted right from the start in such a manner that the final shape of the product is realized at once.

Compared to the prior art, the invention offers the advantage that an earplug is produced which has a smooth and soft outer skin free from pores. According to the state of the art, this was impossible, as is evident from German Utility Model Patent No. 1,905,618, which discloses an earplug made of a foamed core, with this foamed core being coated with an elastic rubber skin.

If, according to the process of the invention, the preshaped product is subdivided into individual sections before the final foaming and cross-linking, it is also possible to produce frontal faces on the earplug which have the same, pore-free, smooth and soft surface structure as the circumferential faces of the plug. Moreover, the individual sections can be additionally shaped to advantage by the use of a compressive pressure to only thereafter be foamed and cross-linked. This offers an opportunity to equip individually shaped earplugs with the advantages of the invention.

The foaming process may be performed with the use of heat and this heat can simultaneously constitute the cross-linking heat. In this case, a single-stage process can be performed in which, after preshaping the product, a finally shaped and cross-linked end product is obtained in a single process step. However, the process according to the invention may also take place in such a manner that the end product is initially foamed and then cross-linked, with high energy radiation, for example, being used for the cross-linking.

A significant feature of the process according to the invention is the final tempering process which cannot be performed with the soft polymers of the prior art. This tempering process, which takes place at temperatures of at least 140° C. and with adjustable time periods, effects the removal of cross-linking agent and expanding agent residues. Such residues are, for example, 1,3-dichlorobenzene, 2,4-dichlorobenzaldehyde, 2,4-dichlorobenzoic acid or benzene, benzaldehyde, benzoic acid; or 1,1,3-trimethyl cyclohexanone, 1,1,3-trimethyl cyclohexanol; or t-butanol, isobutane, t-amyl alcohol, 2-methylbutane or chlorobenzene, 4-chlorobenzaldehyde, 4-chlorobenzoic acid, etc. Such low molecular components are completely removed from the ear plug according to the invention by the tempering treatment above 140° C.

The earplugs produced according to this method, which have a pore-free, smooth and soft outer skin are—as in the prior art—introduced into the human ear passages after a kneading process in which the plug is compressed. Due to the special surface configuration and design, the recovery of the plug results in noticeably reduced pressure on the ear passage so that the wearing of such earplugs becomes more comfortable.

The use of a temperable starting material and the tempering of the product itself in its final shape provide the wearer of such earplugs, in addition to more comfortable use, with a physiologically unobjectionable end product from which the low molecular residues have been expelled. Skin irritations, contact dermatitis, allergies, extensive loss of sebum and brittling of the skin as a result of the residues of isocyanates, polyols, halogen hydrocarbons and activators, are impossible with the use of an earplug produced according to the process of the invention and employing the polysiloxane of the invention.

I claim:

1. Method for producing an earplug of foamed plastic, comprising initially mixing a polysiloxane with at least one additive which is an expanding agent and preshaping the mixture, thereafter heating the mixture to foam the mixture and form its final shape, cross-linking the finally shaped product, and finally subjecting the finally shaped product to a final tempering process.

2. Method according to claim 1, wherein the preshaped product is subdivided into individual sections before the foaming and cross-linking processes.

3. Method according to claim 2, wherein the individual sections are additionally deformed by the use of a compression pressure and are subsequently foamed and cross-linked.

4. Method according to claim 1, wherein the product is subdivided into individual sections after being foamed and cross-linked.

5. Method according to claim 1, wherein the heat for the foaming simultaneously constitutes heat which effects the cross-linking.

6. Method according to claim 1, wherein after the foaming process is performed with the use of heat, and the finally foamed product is cross-linked.

7. Method according to claim 1, wherein the cross-linking is effected by high energy radiation.

8. Method according to claim 1, wherein the foaming heat and the cross-linking heat are below 250° C.

9. Method according to claim 1, wherein the tempering process takes place at a temperature of at least 140° C.

10. Method according to claim 1, wherein the foaming heat and the cross-linking heat are between 90° C. and 160° C.

11. Method according to claim 1, wherein the additives comprise an expanding agent, and the tempering process removes expanding agent residues.

12. Method according to claim 11, wherein the additives comprise a cross-linking agent, and the tempering process removes cross-linking agent residues.

13. Method according to claim 1, wherein the additives comprise at least one expanding agent and at least one cross-linking agent.

14. Method according to claim 1, wherein the expanding agent is selected from azodicarbonamide, benzene sulfohydrazide, diphenyl sulfone-3,3 disulfohydrazide, diphenylene oxide-4,4 disulfohydrazide, trihydrazionotriazine, p-toulene sulfonyl semicarbazide, 5-phenyltetrazole, isatoic acid anhydride, and sodium bicarbonate.

15. The process according to claim 1, wherein the additives comprise a cross-linking agent.

16. Method according to claim 1, wherein the cross-linking agent is selected from benzoyl peroxide, chlorobenzoyl peroxide, t-butyl perbenzoate, dicumyl peroxide and di-t-butyl peroxide.

17. Method according to claim 1, wherein the additives include fillers.

18. Method according to claim 17, wherein the fillers include oxidic or salt-like compounds of calcium, barium, magnesium, aluminum, silicon, titanium, iron, zinc or zirconium.

19. Method according to claim 1, wherein the polysiloxane is represented by the formula:

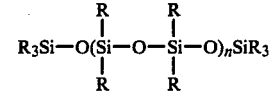

where R is an organic radical.

* * * * *